United States Patent [19]

Audibert et al.

[11] 4,323,559
[45] Apr. 6, 1982

[54] COMPOUNDS DERIVED FROM N-ACETYL-NOR-MURAMYL-L-ALANYL-D-ISOGLUTAMIC ACID AND OTHER COMPOUNDS AND BIOLOGICALLY ACTIVE COMPOSITIONS CONTAINING SUCH COMPOUNDS

[75] Inventors: Françoise Audibert, Neuilly-Sur-Seine; Pierre Lefrancier, Bures-Sur-Yvette, both of France

[73] Assignee: Agencie Nationale de Valorisation de la Recherche (ANVAR), Neuilly sur Seine, France

[21] Appl. No.: 135,928

[22] Filed: Mar. 31, 1980

Related U.S. Application Data

[63] Continuation of Ser. No. 914,073, Jun. 9, 1978, abandoned, which is a continuation-in-part of Ser. No. 516,991, Oct. 22, 1974, Pat. No. 4,186,194.

[30] Foreign Application Priority Data

Oct. 23, 1973 [FR] France .................. 73 37806
Jul. 1, 1974 [FR] France .................. 74 22909

[51] Int. Cl.³ .................. A61K 37/00; C07C 103/52
[52] U.S. Cl. .................. 424/177; 260/112.5 R
[58] Field of Search .................. 424/177; 260/112.5 R

[56] References Cited

U.S. PATENT DOCUMENTS 4,082,735 4/1978 Jones et al. .................. 424/177
4,082,736 4/1978 Jones et al. .................. 424/177
4,094,971 6/1978 Chedid et al. .................. 424/177

FOREIGN PATENT DOCUMENTS 1155134 10/1963 Fed. Rep. of Germany ...... 424/177
2655500 6/1977 Fed. Rep. of Germany ... 260/112.5 R
2358159 7/1976 France .................. 424/177
7413855 10/1974 Netherlands .................. 260/112.5 R

OTHER PUBLICATIONS

Yamamura et al., Gann 67, 867-877 (1976).

Kusumoto et al., Tetrahedron Letters 47, pp. 4287-4290 (1976).
Yamamura et al., Proc. Japan Acad. 52 (1976), 58-61.
Kotani et al., Biken Journal 20, 95-103, 5-10 (1977).
Chedid et al., Proc. Nat'l Acad. Sci. 74 (1977) 2089-2093.
Azuma et al., Infection and Immunity (1976) 14, pp. 18-27.
Adam et al., Biochem. and Biophys. Res. Comm. 72, (1976) 339-346.
Bergey's Manual of "Determinative Bacteriology" 1962, p. 347.
Audibert et al., Cellular Immunology 21, 243-249 (1976).
Kotani et al., Biken Journal 18, 105-111 (1975).

*Primary Examiner*—Delbert R. Phillips
*Attorney, Agent, or Firm*—Weiser, Stapler & Spivak

[57] ABSTRACT

The invention relates to water-soluble biologically active agents, having anti-infectious and adjuvant properties. They have the general formula

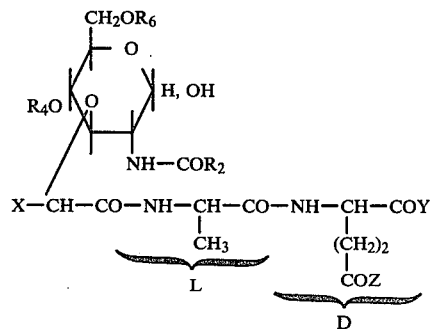

wherein X, Y, Z, $R_2$, $R_4$ and $R_6$ have the meanings defined in claim 1. The invention also relates to pharmaceutical compositions containing these compounds in association with a pharmaceutical vehicle, particularly an oil-free one.

7 Claims, No Drawings

COMPOUNDS DERIVED FROM N-ACETYL-NOR-MURAMYL-L-ALANYL-D-ISO-GLUTAMIC ACID AND OTHER COMPOUNDS AND BIOLOGICALLY ACTIVE COMPOSITIONS CONTAINING SUCH COMPOUNDS

This is a continuation of application Ser. No. 914,073, filed June 9, 1978, now abandoned, which in turn is a continuation in part of Ser. No. 516,991 filed on Oct. 22, 1974, now Pat. No. 4,186,194.

The invention relates to water-soluble biologically active agents, which are more particularly effective as systemic, particularly anti-infectious agents among others as agents capable of increasing the resistance of the host's organism to pathogenic germs. They are also active as immunological regulants, particularly adjuvants for enhancing the immune responses to antigens, most preferably when administered to a host in the form of an oil-free composition.

The invention also relates to pharmaceutical compositions which contain these agents in association with a pharmaceutical vehicle, as well as to the process for their preparation.

The invention also relates to a method for preventing or combating infection, which comprises administering to a warm-blooded host the compounds hereinafter defined. The method can also be termed as one for increasing the resistance of the host's organism to pathogenic germs.

The compounds of the invention are formed of 2-(2-acetamido-2-deoxy-3-O-D-glucopyranosyl)-D-alkanoyl-peptide derivatives.

Compounds having the above mentioned activity have been disclosed and claimed in copending applications Ser. No. 775,215 filed on Mar. 7, 1977 by Audibert et al and Ser. No. 847,673 filed on Nov. 1st, 1977 by Audibert et al.

The compounds according to the invention have the general formula

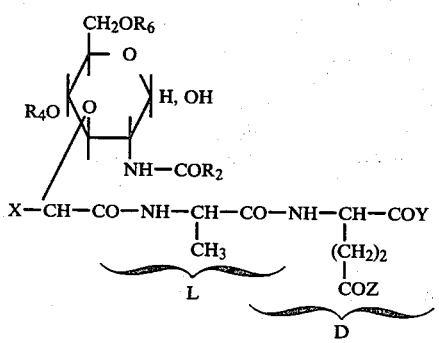

wherein:
X is either hydrogen or a methyl group;
Y is hydroxy; alkoxy comprising from 1 to 4 carbon atoms or amino (—NH$_2$);
Z is hydroxy; alkoxy comprising from 1 to 4 carbon atoms, with the proviso that Y is then not amino; amino (—NH$_2$) with the proviso that Y is then neither amino, nor alkoxy; or a group comprising from 1 to 4 aminoacyl residues selected from levorotatory aminoacyl residues or glycyl, identical or different from one another;
R$_2$ is a group comprising 1 carbon atom;
each of R$_4$ and R$_6$, which are identical or different, is hydrogen or a group comprising from 1 to 4 carbon atoms with the proviso that simultaneously R$_4$ and R$_6$ are not both hydrogen when X and R$_2$ are both methyl and, when Z is a group comprising aminoacyl residues, the free carboxylic group of the last aminoacid is either free or amidated.

In the subsequent discussion:
the following group

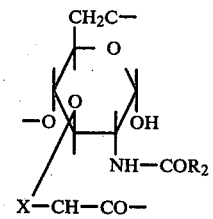

will also be designated as a N-acyl-muramyl or N-acyl-nor-muramyl group, depending upon whether X is methyl or hydrogen; when R$_2$ is methyl, this designation will thus become: N-acetyl-muramyl and N-acetyl-nor-muramyl respectively, also hereafter abbreviated as Mur-HAc and norMur-HAc;
and the following group

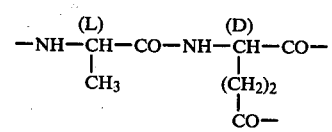

will be abbreviated as L-Ala-D-Glu, it being understood that this abbreviated designation will be completed by the chemical groups fixed to the two carboxyl functions; the chemical substitution group on the $\gamma$ carboxyl function of the glutamic residue being indicated within brackets.

R$_2$ is particularly a methyl or hydroxymethyl group.

When, in the above formula, Z comprises at least one aminoacyl residue, the one which is the remotest from the above mentioned glutamic residue has a carboxylic group which may be either free or substituted by an amino group or by an alkoxy group comprising from 1 to 4 carbon atoms. Z then advantageously comprises L-alanyl, L-lysyl groups or both.

Preferred compounds are designated hereinafter by way of example:
norMur-NAc-L-Ala-D-Glu-OH;
norMur-NAc-L-Ala-D-Glu(NH$_2$)-OH;
norMur-NAc-L-Ala-D-Glu(OH)-NH$_2$;
norMur-NAc-L-Ala-D-Glu(OH)-OCH$_3$;
norMur-NAc-L-Ala-D-Glu(OCH$_3$)-OCH$_3$;
4,6-Di-O-acetyl-norMur-NAc-L-Ala-D-Glu(OH)-NH$_2$;
6-O-Succinyl-norMur-NAc-L-Ala-D-Glu(OH)-NH$_2$;
norMur-NAc-L-Ala-D-Glu(L-Lys-OH)-NH$_2$;
norMur-NAc-L-Ala-D-Glu(L-Lys-NH$_2$)-NH$_2$;
norMur-NAc-L-Ala-D-Glu(L-Lys-L-Ala-OH)-NH$_2$;
4,6-Di-O-acetyl-Mur-NAc-L-Ala-D-Glu(OH)-NH$_2$;
6-O-Succinyl-Mur-NAc-L-Ala-D-Glu(OH)-NH$_2$;
4,6-Di-O-acetyl-Mur-NAc-L-Ala-D-Glu(L-Lys-OH)-NH$_2$;
4,6-Di-O-acetyl-Mur-NAc-L-Ala-D-Glu(L-Lys-L-Ala-OH)-NH$_2$;
6-O-Succinyl-Mur-NAc-L-Ala-D-Glu(L-Lys-OH)-NH$_2$;

6-O-Succinyl-Mur-NAc-L-Ala-D-Glu(L-Lys)-L-Ala-OH)-NH₂;

Mur-NAc-L-Ala-D-Glu(L-Lys-OCH₃)-NH₂.

The invention also concerns more specifically the compounds of the above said type in which an N-glycolyl residue is substituted for the N-acetyl residue of the N-acetyl-muramyl or N-acetyl-nor-muramyl group.

In order to prepare the compounds according to the invention one may prepare, in a first stage, a reactive derivative of the desired L-alanyl-D-glutamic residue, which carries any of the above defined substituents on the $\alpha$ and/or $\gamma$ carboxylic groups, whenever appropriate, on the one hand, and the Mur-NAc or norMur-NAc acids, whose functional groups which must not react have first been protected, on the other hand, and then, in a second stage, effect the coupling of these two derivatives. The protecting groups are finally removed, to free the previously blocked functions.

It is also possible to effect the synthesis of these compounds by first coupling a derivative of the Mur-NAc or norMur-NAc acid with a derivative of L-alanine, then by coupling the resulting product with the equivalent derivative of the glutamic acid residue which carries the adequate substituents when appropriate, according to the processes generally used in peptide synthesis.

The N-acetyl residue of the N-acetyl-muramyl or N-acetyl-norMur acid may first be converted beforehand into the N-glycolyl corresponding derivatives. This may be achieved for instance by the process steps which comprise hydrolysing the acetyl group (the other functions, particularly in the 1-, 4- and 6- positions being protected) by means of a strong alkaline compound, for instance as disclosed by P. H. GROSS and R. W. JEANLOZ (J. Org. Chem., 1967, 32, 2761), reacting the deacetylated derivative obtained with benzyloxyacetic chloride and subjecting the ether derivative obtained to catalytic hydrogenolysis, to form the N-glycolyl derivative at the end of the synthesis of the glycopeptide, for instance according to the method of LEFRANCIER et al (Int. J. Peptide Protein Res., 1977, 9, 249). The substitutions in the 4- and 6- positions may be achieved by methods which are conventional in the art of carbohydrates. When the contemplated substitution groups differ from each other, the substitution reactions will be carried out successively. Those of the groups which are not to be substituted in the course of a substitution step will be protected temporarily by conventional blocking groups. When benzyl groups or benzylidene blocking groups are used, the latter may be removed upon refluxing in the presence of acetic acid and further subjecting the reactants to catalytic hydrogenolysis, as disclosed for instance by MERSER et al (Biochem. Biophys. Res. Commun., 1974 466, 1316) or by catalytic hydrogenolysis by the method of LEFRANCIER et al already referred to hereabove.

The introduction of the substitution groups can be carried out by conventional procedures, particularly upon resorting to the acylating agent corresponding to the desired substitute (anhydride, acid, chloride, etc.).

It should be mentioned that the 6- position is more reactive than the 1- and 4- positions, so that the acylation of that position may be carried out without blocking the other positions, provided the amount of substituting agent be that required for the substitution of that sole position.

A particular example of preparation of 6- substituted derivatives is indicated in an article published by KUSUMOTO et al (Tetrahedron Letters, 1976, 47 4237).

The substitutions on the osidic group may be carried out either before or after the fixation of the above mentioned L-alanyl-D-glutamic derivative, possibly carrying any of the appropriate substituents on either the $\alpha$ or $\gamma$ carboxylic groups of the glutamic residue, or both.

The chemical side of the invention will be further illustrated hereafter by the disclosure of preferred examples of production of some of the preferred derivatives according to the invention.

I—The production of the 2-(2-acetamido-2-deoxy-3-O-D-glucopyranosyl)-acetyl-L-alanyl-D-isoglutamine(norMur-NAc-L-Ala-D-Glu(OH)-NH₂

The process for making that compound comprises two steps. The first step consists of carboxymethylating the 2-acetamido-2-deoxy-glucopyranoside in the 3- position of the nucleus and the second step consists of fixing the peptidic chain. While these operations are carried out, the functions which must not react are protected by blocking groups which are removed thereafter.

(a)
Benzyl-2-acetamido-4,6-O-benzyliden-3-O-carboxymethyl-2-deoxy-β-D-glucopyranoside (I)

1 g (2.5 m moles) of benzyl-2-acetamido-4,6-O-benzyliden-2-deoxy-β-D-glucopyranoside (P. H. Gross & R. W. Jeanloz, J. Org. Chem. 1967, 32, 2761) is dissolved in 112.5 ml of anhydrous dioxane and deperoxydated at 90° C. After addition of 350 mg (7.37 moles) of a 50% sodium hydride suspension in oil, the mixture is stirred for two hours at 90° C., and 4.4 m moles of chloroacetic acid are then added. After 1 hour at 85° C. a second addition of 700 mg of the suspension of sodium hydride is made. The mixture is then left overnight at 65° C. exactly, under stirring.

After cooling in an ice bath, the sodium hydride in excess is destroyed upon adding 25 ml of water. Two phases form. The upper phase is removed, filtered, then concentrated. The residue obtained is dissolved in water. The aqueous solution is extracted several times with chloroform, then acidified at 0° C. with hydrochloric acid 2.5 M up to pH 3. The precipitate obtained is immediately filtered off, washed with water, then dried. It is then crystallized in methanol at a temperature between cold and warm. One obtains 1.2 gr (yield of 67.2%) of product (I) whose melting point is of M.P. 237.5°–238° C. and the rotatory power $[\alpha]_D^{25} = -80°$ (c=0.4 in pyridin). The elementary analysis of the product is:

| C₂₄H₂₇O₈N (457.48) | C | H | N |
| --- | --- | --- | --- |
| calculated % | 63.01 | 5.95 | 3.06 |
| found % | 62.36 | 5.80 | 2.96 |

(b)
2(benzyl-2-acetamido-4,6-O-benzyliden-2-deoxy-3-O-β-D-glucopyranosyl)-acetyl-L-alanyl-D-isoglutamine benzyl ester (II)

407.46 mg (1 m mole) of benzyl ester of the t. butyloxycarbonyl-alanyl-D-isoglutamine (BOC-L-Ala-D-Glu(OBzl)-NH₂), prepared according to the method disclosed by P. Lefrancier and E. Bricas in Bull. Soc.

Chim. Biol. 1967, 49, 1257, are treated by 3 ml of a normal solution of hydrochloric acid in ice-acetic acid. 30 minutes thereafter, the reaction mixture is concentrated to dryness and desiccated. The oil obtained is taken up in 25 ml of an acetonitrile-dimethylformamid mixture (2/1 volume to volume). The mixture cools down to 0° C. and one adds 0.141 ml (1 m mole) of triethylamin. The solution so obtained is poured, under stirring, at 0° C. in a suspense which had been prepared 1.5 hour earlier, of 475.5 mg (1 m mole) of (I), of 0.141 ml (1 m mole) of triethylamin, and of 253.28 mg (1 m mole) of the Woodward reactive (N-ethyl-5-phenyl-isoxazolium-3'sulfonate) in 25 ml of the preceding acetonitrile-dimethylformamid mixture. After one night at ambient temperature, the reaction mixture is concentrated to a minimum and the product is precipitated by a 10% citric acid solution. It is filtered, abundantly washed with water and dried. One obtains 665 mg of product, i.e. a yield of 89%. 302 mg of this product have been purified on a silicate column, by elution with the chloroformmethanol mixture (6/1 volume to volume), then crystallized in a methanol-acetone-ether mixture. One recovers in that manner 225 mg of the product (II) whose melting point is M.P 240°–243° C. and the rotatory power $[\alpha]_D^{25} = -56°$ (c=0.55 acetic acid). Elementary analysis of this product is as follows:

| $C_{39}H_{46}O_{11}N_4$ | C | H | N |
| --- | --- | --- | --- |
| calculated % | 62.72 | 6.21 | 7.5 |
| found % | 62.75 | 6.24 | 7.48 |

(c) 2(benzyl-2-acetamido-2-deoxy-3-O-D-glucopyranosyl)-acetyl-L-alanyl-D-isoglutamine benzyl ester (III)

360 mg of (II) are treated by 30 ml of a 60% acetic acid solution in a refluxing water-bath, for 1 hour. The reaction mixture is then concentrated to dryness and dried. The residue obtained is purified on a silica gel column by elution with the chloroform-methanol mixture (5/1 volume to volume). One recovers 135 mg, thus a yield of 42.5% of the product (III) whose melting point is M.P. 230°–231° C.

(d) 2(2-acetamido-2-deoxy-3-O-D-glucopyranosyl)-acetyl-L-alanyl-D-isoglutamine (IV)

130 mg (0.19 m mole) of (III) are hydrogenated, for 3 hours, in the presence of Pd on charcoal (5%) in iced acetic acid. After filtration, the reaction mixture is concentrated to dryness. The product is precipitated in the methanol-ether mixture. One obtains in such manner 94.4 mg of product (IV) which exhibits a melting point M.P. 160°–165° C. and whose elementary analysis is as follows:

| $C_{18}H_{30}O_{11}N_4$ (478.47) | C | H | N |
| --- | --- | --- | --- |
| calculated % | 62.72 | 6.21 | 7.5 |
| found % | 62.75 | 6.24 | 7.48 |

II—Preparation of 4,6-di-O-acetyl-Mur-NAc-L-Ala-D-Glu (OH)-NH$_2$ 1-benzyl-4,6-benzyliden-Mur-NAc-L-Ala-D-isoglutaminyl benzylester are refluxed in the presence of 60% of acetic acid for one hour at 100° C. 1,α benzyl-Mur-NAc-L-Ala-D-isoglutaminyl benzylester is thus obtained.

This compound solubilised in pyridin is then treated by two equivalents of acetic anhydride. The desired compound is obtained upon hydrogenolyzing the derivatives bearing the above mentioned benzyl groups with hydrogen in the presence of charcoal-supported palladium and upon purifying chromatographically a solution of the compound obtained in a chloroform-methanol mixture on a column of silica gel.

The compound obtained has a melting point of 159°–162° C. and an $[\alpha]_D^{25}$ of +48.8 in anhydrous acetic acid.

III—Preparation of 6-O-succinyl-Mur-NAc-L-Ala-D-Glu, (OH)-NH$_2$

One uses the same starting compound and carries out the same subsequent operations as in example II except that the final acylation is divided into 2 successive steps, first with one equivalent of succinic anhydride, in pyridin.

The compound finally obtained has a melting point of 138°–142° C. and an $[\alpha]_D^{25}$ of +35.3 in pyridin.

The invention also relates to the physiologically active, particularly pharmaceutical compositions, containing the said compounds together with physiologically acceptable carriers or vehicles, such compositions being useful, particularly for the prevention or treatment of infectious diseases, particularly bacterial, viral and parasitic infections. They also have other immunoregulating, particularly adjuvant, properties, thus are effective to enhance or restore in non specific a manner the immune responses of warm-blooded hosts to antigens or any kind of agent capable of eliciting an immune response, even if only in the presence of an immuno-logical adjuvant.

One of the interests of the new products according to the invention is that their physiological activity is not dependent upon the nature of the carriers used for their administration. In particular, it is not necessary, when these products are injected, to use compositions containing an oily phase, particularly in conjunction with their immunoregulating activities. These compositions can be adapted for their being administered orally or parenterally, and especially by injection.

Preferred injectable compositions thus contain an effective dose of any of the compounds of the invention. Sterile solutions in an aqueous, preferably isotonic, phase, such as asline isotonic solutions or isotonic solutions of glucose, are advantageously used for this purpose. This is of course not restrictive; a simple solution in distilled water can also be used. It is nevertheless also possible to use injection media containing an oily phase, especially water-in-oil emulsions. Such emulsions are obtained in particular with metabolisable vegetable oils, such as are described in U.S. Application Ser. No. 656,738 filed on Feb. 9, 1976.

The medicinal compositions of the invention may also be presented in various forms, by using for this purpose vehicles suitable for the selected method of administration. For example, compositions will be used in the form of cachets, compressed tablets or gelatine-coated pills, for oral administration, and aerosols or gels for the application to mucous membranes.

The compounds of the invention may also be in lyophilised form so as to permit the extemporaneous preparation of the medicinal compositions.

A pharmaceutically advantageous form comprises unit doses 10 to about 2000 μg, preferably 100 to 800 μg of the adjuvant product according to the invention, for instance about 400 μg.

The invention also includes medicinal compositions in which the products of the invention are associated with an immunising agent, especially a weak or attenuated or also highly purified vaccinating antigen, although the latter may also be administered separately, even under a form suitable for administration by another route.

The compounds of the invention are not antigenic; in fact, they do not induce any delayed sensitivity reaction in the case of the guinea-pig previously sensitised by means of the Freund complete adjuvant. They have substantially no hyperthermising action in the rabbit at doses under which they are already capable of exerting an efficient anti-infectious action. They are not active in the Limulus test and their injection does not cause the death of adrenalectomised mice although the latter are rendered extremely sensitive to the lethal effect of the endotoxins by this operation. These results show that these compounds are completely deprived of endotoxic character. They have the advantage of being active as anti-infectious agents in the absence of an oily phase, whether the administration is made parenterally or orally, as compared to agents which, like bacterial lipopolysaccharides, are only active when administered parenterally.

An important advantage of the anti-infectious of the compounds of the invention lies in their possible action against pathogenic germs which have become resistant to antibiotics as a consequence of antibiotic-based treatments.

(1) The following tests illustrate the anti-infectious properties of compounds representative of the class according to the invention.

In the preliminary tests, an experimental method was established permitting the anti-infectious character of the products to be shown. It has thus been shown that a dose of $10^4$ Klebsiella pneumoniae, injected intramuscularly in mice, causes a progressive death rate of a large part, if not of all the animals in the week following inoculation. After eight days, those animals which survived were considered as cured.

For these tests, hybrid mice (C57B1/6×AKR)F1, reared at the PASTEUR INSTITUTE, from strains coming from the breeding of the C.N.R.S. at Orleans, were used.

The infection was caused by means of a culture of 16 hours of Klebsiella pneumoniae, strain of capsular type 2, biotype d, in a medium for pneumococcus (No. 53515, PASTEUR INSTITUTE).

The preparations injected before or at the moment of the infection were always diluted in apyrogenic physiological solution, at the rate of 0.2 ml for parenteral administration and 0.5 ml for oral administration. The conrols received either the solution alone or a solution of Mur-NAc-L-Ala-D-Glu(OH)-NH$_2$ for comparison purposes.

The results are reported in Table I, which indicates the doses, times and methods of administration of the products studied. The percentage of protection expresses the difference of the percentages of survivors in the groups of treated animals with respect to the corresponding control groups (those which received the above said solution alone). The letter D stands for "Day".

TABLE I

| Infection by K. pneumoniae | | Treatment | | | | No. of mice | % survival | | | % protection |
|---|---|---|---|---|---|---|---|---|---|---|
| Administr. | Dosis | Time | Compound | Administr. | Dosis μg | D0 | D + 3 | D + 5 | D + 10 | |
| im. | $1,5 \times 10^4$ | −24 h | controls | iv. | — | 32 | 38 | 16 | 16 | |
| " | " | " | Mur-NAc-L-Ala-D-Glu(OH)—NH$_2$ | " | 100 | 24 | 83 | 66 | 60 | 47 |
| " | " | " | nonMur-NAc-L-Ala-D-Glu(OH)—NH$_2$ | " | 100 | 32 | 78 | 64 | 60 | 47 |
| " | $2 \times 10^4$ | " | controls | " | — | 32 | 50 | 47 | 16 | |
| " | " | " | 4,6-di-O-acetyl-Mur-NAc-L-Ala-D-Glu(OH)—NH$_2$ | " | 100 | 32 | 97 | 84 | 63 | 47 |
| " | " | " | controls | " | — | 32 | 50 | 38 | 19 | |
| " | " | " | 6-O-Succinyl-Mur-NAc-L-Ala-D-Glu(OH)—NH$_2$ | " | 100 | 32 | 100 | 91 | 63 | 44 |

These results are thus highly representative of the must remarkable efficiency of the compounds of the invention. The similitude in magnitude of activity of the Mur-NAc and norMur-NAc derivatives is noteworthy.

(2) The following tests show that the compounds according to the invention also exhibit a remarkable adjuvant activity when administered in the form of an aqueous phase.

In the series of tests of which the results are indicated hereafter, the influence of the active principle according to the invention was assessed as bearing on the anti-albumin antibody rate, particularly under the following conditions.

Groups of 8 two-month-old Swiss mice received by subcutaneous injection (SC) or orally (PO) 0.5 mg of antigen constituted by the bovine serum albumin (BSA) with or without the substance tested in an isotonic saline solution. This large dose of antigen, because of its closeness to the limit paralysing dose with respect to the immunising response, elicits but a weak or no immune response in the controls; it therefore constitutes a severe criterion for showing the activity of an adjuvant substance. Thirty days later, the mice received, by the same method of administration, a further dose containing 0.1 mg of the same antigen.

The proportion of antibody was determined by passive hemagglutination by using sheep red blood cells treated with formalin and coated with the antigen studied according to the method described by A. A. HIRATA and M. W. BRANDISS (J. Immunol., 100, 641–648, 1968). Blood samples were taken 14, 28, 34 and 36 days after the first injection.

Table II shows the results obtained in the test as hereabove described with norMur-NAc-L-Ala-D-Glu(OH)-NH$_2$ the active principle, compared to the results obtained with controls, on the one hand, and, for purpose of comparison, with Mur-NAc-L-Ala-D-Glu(OH)-NH$_2$, on the other hand.

TABLE II

|  | Admin-istra-tion | Titer of antibody | | |
| --- | --- | --- | --- | --- |
|  |  | 28th day | 34th day | 36th day |
| BSA controls | S.C. | <3 | <3 | 6 |
| BSA + Mur-NA-L-Ala-D-Glu(OH)-NH$_2$ (100 μg) | S.C. | 25 | 50 | 400 |
| BSA + Normur-NAc-L-Ala-D-Glu(OH)-NH$_2$ (100 μg) | S.C. | 25 | 50 | 350 |

Dose BSA 0.5 mg/animal

These results show that, when administered in isotonic saline solution, the norMur-NAc-derivatives are liable of inducing an immune response of the same order of magnitude than the corresponding Mur-NAc-derivatives.

This applies to the 4-O- and 6-O- substituted derivatives too.

We claim:

1. A biological composition which comprises a biologically acceptable carrier and, in a biologically effective amount, a water-soluble, biologically active compound which is an adjuvant and anti-bacterial in vivo of the formula:

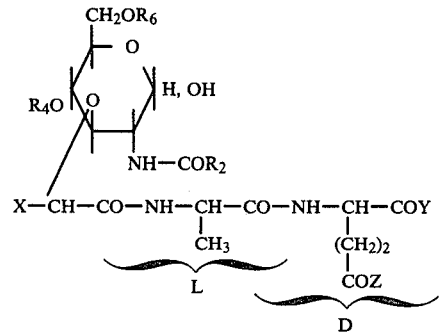

wherein X is hydrogen,
R$_2$ is methyl, R$_4$ is hydrogen R$_6$ is hydrogen and Y is amino when Z is hydroxyl, or Y is methoxy when Z is methoxy.

2. A method which comprises controlling bacterial infection in vivo- by administering to a warm-blooded host, in an effective amount, a systemic biologically active composition which is water-soluble, and anti-bacterial in vivo and adjuvant, which composition comprises a biologically acceptable carrier and an in vivo anti-infectious and adjuvant compound of the formula:

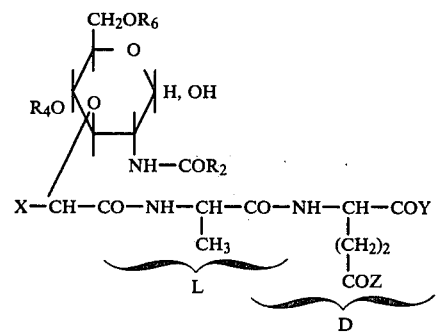

wherein X is hydrogen,
R$_2$ is methyl, R$_4$ is hydrogen, R$_6$ is hydrogen and Y is amino when Z is hydroxyl, or Y is methoxy when Z is methoxy.

3. The method of claim 2 wherein Z and Y are both methoxy or wherein Y is amino and Z is hydroxyl.

4. The composition of claim 1 wherein the compound is Nor-Mur-NAc-L-Ala-D-Glu-(OCH$_3$)-OCH$_3$.

5. The composition of claim 1 wherein the compound is Nor-Mur-NAc-L-Ala-D-GluNH$_2$(-OH).

6. The method of claim 2 wherein the compound is Nor-Mur-NAc-L-Ala-D-GluNH$_2$(OH).

7. The method of claim 2 wherein the compound is Nor-Mur-NAc-L-Ala-D-Glu-(OCH$_3$)-OCH$_3$.

* * * * *